United States Patent [19]

Crump et al.

[11] 4,115,130

[45] Sep. 19, 1978

[54] BIOCIDAL COMPOSITIONS

[75] Inventors: Ronald Alfred Crump, Horsham; Colin Christopher McCain, Horley, both of England

[73] Assignee: The British Petroleum Company Limited, Sunbury-on-Thames, England

[21] Appl. No.: 775,895

[22] Filed: Mar. 9, 1977

[30] Foreign Application Priority Data

Mar. 15, 1976 [GB] United Kingdom ............... 10244/76

[51] Int. Cl.$^2$ ................................................ C09D 5/16
[52] U.S. Cl. ..................................... 106/15 R; 106/16; 106/17; 106/18; 106/272; 424/288
[58] Field of Search .................. 106/15 R, 16, 17, 18, 106/272; 252/455 Z; 424/288

[56] References Cited

U.S. PATENT DOCUMENTS

| | | | |
|---|---|---|---|
| 3,100,719 | 8/1963 | Dunn et al. | 106/15 R |
| 3,234,032 | 2/1966 | Leebrick et al. | 106/15 R |
| 3,708,573 | 1/1973 | Yoshinaga et al. | 71/79 |
| 3,835,032 | 9/1974 | Dolbear et al. | 252/455 Z |
| 3,888,683 | 6/1975 | Horai et al. | 106/15 AF |

*Primary Examiner*—Lorenzo B. Hayes
*Attorney, Agent, or Firm*—Morgan, Finnegan, Pine, Foley & Lee

[57] ABSTRACT

A biocidal composition suitable for use in marine anti-fouling coatings is a water-insoluble mineral having an internal pore structure, containing, within the pores a biocidal compound effective against marine growth. Preferred minerals are zeolites, particularly synthetic faujasites, and porous silicas; preferred biocidal compounds are organo-tin compounds.

The compounds may be incorporated into anti-fouling paints e.g. epoxy, epoxy-coal tar and chlorinated rubber paints or wax coatings.

9 Claims, No Drawings

BIOCIDAL COMPOSITIONS

This invention relates to biocidal compositions, e.g. anti-fouling compositions suitable for preventing marine growth on underwater surfaces.

Biocidal compounds effective against marine growth include metal compounds, e.g. compounds containing tin, copper, zinc, nickel, cobalt, manganese or mercury, and organic compounds having an active structure containing S, Cl, N or O atoms. Among the most effective biocidal compounds for preventing marine growth on underwater surfaces e.g. ships hulls, are copper compounds, e.g. cuprous oxide and tin compounds e.g. organo-tin compounds of general formula $$R_3 SnX$$

where $R$ is a lower hydrocarbyl group and $X$ may be one of a variety of anionic radicals including oxide, sulphide, halide and organic acid radicals. Trialkyltin oxides or sulphides are commonly used compounds which are incorporated into anti-fouling marine coating compositions e.g. anti-fouling paints.

The marine coating compositions aim to release the anti-fouling compounds or radicals into the water in a steady controlled fashion so that the compositions have a long effective life but it is generally accepted that there is still room for improvement in controlling the release. For example, E. J. Dyckman et al commented in an article in the Naval Engineers Journal, December 1973, pages 33 to 37 that "anti-fouling paint formulations containing e.g. tributyltin oxide still leach these agents at a rate in excess of the lethal concentration needed for fouling prevention", and in the Australian OCCA Proceedings and News, July 1973, page 17, A. T. Phillip said "It is thought that tributyltin oxide behaves like a solvent and diffuses rapidly to the surface of the film so that, after an initial period of effectiveness, its activity falls off with time".

The present invention is concerned with a composition giving a slower release of biocides such as organo-tin compounds.

According to the present invention a biocidal composition, suitable for use in anti-fouling marine coatings comprises a water-insoluble mineral having an internal pore structure and, included within the pores, a biocidal compound effective against marine growth.

The biocidal compound may be a metal compound e.g. a copper or tin compound or an organic biocide, or an combined organo-metal compound, but is preferably an organo-tin compound of general formula $$R_3 SnX$$

where $R$ is a hydrocarbyl group with from 1 to 10 carbon atoms, and $X$ is an anion. The hydrocarbyl group may be alkyl, e.g. butyl or propyl, or aryl e.g. phenyl. $X$ may be an oxygen, sulphur, halide, or organic acid anions, the organic acid anion preferably having from 1 to 5 carbon atoms e.g. acetate. As will be discussed in more detail hereafter the hydrocarbyl group and anion may be selected in relation to the pore size of the mineral to control and vary the rate of release.

The term mineral is to be understood as including both natural and synthetic materials. The best-known minerals having an internal pore structure are the zeolites. Zeolites are crystalline metal-alumino-silicates which can be dehydrated without loss of crystallinity and which have exchangeable cations. Several of them are already well known as desiccants, selective adsorbents and catalysts. The effective size of the pores and hence the maximum size of the molecules which can be adsorbed depends on the particular crystal structure of the zeolite and the nature of the cation.

Zeolites having effective pore diameters ranging from 3Å to at least 10Å are known. Having regard to the size of the organo-tin compounds, the preferred zeolites are the synthetic fajuasites known as Zeolites X and Y which have an effective pore diameter of 9–10Å. Since the compositions will be in contact with sea-water, sodium zeolites are preferred to avoid any complications of cation-exchange.

Another suitable type of mineral is silica having an internal pore structure. A range of silicas having average pore diameters of from 10 to 250Å are commercially available. These silicas are also characterised by small average particle sizes e.g. of less than 50 microns, high BET surface areas of e.g. above 150 m$^2$/g and high pore volumes of at least 0.7 cc/g. as measured by the method of water porosimetry described in U.K. Patent Specification No. 1415649. They may be prepared by synthetic precipitation from e.g. calcium silicate solution or by hydrolysis of silicon tetrachloride in an oxygen-hydrogen flame. Suitable silicas are those sold by Joseph Crosfield & Sons Ltd. under the trade mark "Neosyl" and by Degussa A. G. and the Dow Corning Corpn. under the trade mark "Aerosil". Further information on porous silicas may be found in the book "The Structure and Properties of Porous Materials" by D. H. Everett and F. S. Stone, published in 1958 by Butterworths, London.

The mineral may be used in the form of fine particles preferably having an average particle size below 200 microns and more particularly below 50 microns.

The biocidal compound chosen and the mineral chosen should obviously be related in terms of molecular diameter and pore diameter for successful inclusion in the pores and for a regulated rate of leaching. For the 9–10Å pore diameter zeolites the included molecule must be relatively simple to ensure a diameter below 9–10Å. A wider range of biocidal compounds can be included in the silicas because of the larger pore diameter. However even with pores of only 9–10Å diameter, preferred biocides such as tributyl tin oxide, tributyl tin chloride, tributyl tin acetate and the corresponding tin propyl derivatives can be incorporated.

As indicated earlier the type of biocide in relation to the mineral and its pore diameter affects the rate of leaching. Thus in tests using a 10Å zeolite immersed in sea water it was found that tributyl tin chloride was released at twice the rate of tributyl tin acetate and that a further reduction in the molecular diameter by the use of tripropyl tin chloride increased the release rate twenty fold. It was also found that tributyl tin chloride was released more quickly from a 25Å average pore diameter silica than from a 10Å pore diameter zeolite. Consequently a particular feature of the present invention is the control attainable in the rate of leaching, which is quite independent of any additional control available through the porosity of the coating in which the mineral-biocide composition may be placed.

The biocidal compounds can be simply and easily incorporated into the mineral by immersing the mineral in a liquid consisting of or containing the compounds. Compounds which are not liquids at ambient temperature may be heated to melt them and incorporated in the molten state or they may be dissolved in a suitable solvent, preferably a non-aqueous solvent which itself is capable of being included within the pores and which can be removed by heating leaving the compound within the pores. Examples of suitable solvents are $C_1$-$C_4$ alcohols or ketones and $C_6$-$C_8$ aromatics.

The amount of any given compound which can be included within any given mineral can readily be determined by a preliminary experiment e.g. by immersing the mineral in an excess of the liquid, allowing the adsorption to reach equilibrium, removing excess liquid and measuring the uptake. Thereafter the amount used may be slightly less than the maximum adsorbable amount. Amounts of biocide incorporated may range from 1 to 100% wt by weight of the mineral depending on the compound and the mineral used. With the preferred organo-tin compounds the amount is preferably from 50-100% wt by weight of the mineral.

The mineral should be heated before the incorporation of the compound to remove any water in the pores or is otherwise used in dehydrated form.

The compositions of the present invention may be used in any situation where the controlled release of biocidal compounds is required, e.g. in anti-fouling marine coating compositions and the present invention includes anti-fouling marine coating compositions containing a mineral/biocidal compound composition as hereinbefore described. Having regard to their preferred fine particle size, the mineral/biocidal compound compositions can be readily incorporated into any of the known anti-fouling marine coating compositions including anti-fouling paints and wax coatings.

A preferred use of the composition is, in fact, in wax coatings for underwater surfaces such as ships' hulls. U.K. Pat. No. 1,479,702 and U.S. Pat. No. 4,020,200 describe and claim a process for coating a surface capable of underwater use with wax characterised in that the wax coating has a thickness of from 5 to 500 micrometres and contains at least one biocide dispersed or dissolved in the wax which is effective against marine weed and/or shell growth when so dispersed or dissolved. U.K. Pat. No. 1,479,701 and U.S. application Ser. No. 735,617 filed Oct. 26, 1976, which is a continuation of U.S. application Ser. No. 556,447 filed Mar. 7, 1975 (now abandoned) and 11189/74 describes and claims a process for coating a surface intended for underwater use, characterised in that the wax is applied as an aqueous dispersion of a wax.

Wax coatings applied as an aqueous dispersion and containing a biocide are potentially useful alternatives to anti-fouling paints. The use of an aqueous dispersion gives the finished coatings a certain porosity which allows the biocide to be gradually released. Incorporating the biocide in a mineral according to the present invention gives a further control over the rate of release. It also provides advantages in the preparation and application of the coatings and in the amount of biocide that can be incorporated. Most biocides are polar and hence can affect the preparation of aqueous wax dispersions and their stability. This in its turn can limit the amount of biocide that can be incorporated. By containing the biocide in a mineral, interaction between the biocide and the compounds used to form and stabilise the dispersion is reduced allowing a larger amount of biocide to be incorporated. As previously indicated the preferred minerals can contain up to their own weight of biocide and the present invention includes wax coatings containing from 2 to 50% wt of mineral, preferably 5 to 20% wt, and 1 to 30% wt of biocide preferably 4 to 15% wt by weight of the finished water-free coating.

The invention also has potential for use in anti-fouling paints based for example on epoxy resins, epoxy-coal tar resins or chlorinated rubber. Again, the incorporation of the biocide in a mineral reduces any interaction between paint and biocide during preparation and storage and also provides additional control on the rate of release of biocide. In tests it was found for example, that a paint based on epoxy resin was considerably less porous than one based on an epoxy-coal tar resin. Good anti-fouling properties were obtained with both paints, however, by choosing a relatively slow release rate mineral/biocide combination for the more porous paint and a relatively high release rate mineral/biocide combination for the less porous paint.

The preferred amounts of mineral and biocide in paint coatings may be the same as for the wax coatings given above.

The invention is illustrated by the following examples.

EXAMPLE 1

1.9 g of tributyltin acetate (MP 81°-84° C) was heated and the temperature maintained at 100° C. 4 g of powdered zeolite type 13X (ex W. R. Grace Ltd.) was added slowly with agitation. All the liquid was adsorbed and a mobile free flowing powder was obtained.

EXAMPLE 2

2 mls of a methanol solution of tributyltin acetate containing 20% by weight of the tin compound was added to 4 g of powdered zeolite type 13X as used in Example 1. The mobility of the powder was maintained. The solvent was subsequently removed by heating where-upon further sequential additions of the solution were possible to raise the content of the tin compound in the sieve.

EXAMPLE 3

2 mls of tributyltin oxide was added directly 4 gms of the powdered zeolite as used in Example 1. Complete adsorption of the tin compound was achieved and the mobility of the powder maintained.

EXAMPLE 4

0.18 g of zeolite impregnated with tributyltin acetate ($\sim$32% wt by weight of zeolite) prepared as in Example 1 and 0.25 g of zeolite impregnated with tributyltin acetate ($\sim$23% wt by weight of zeolite) prepared as in Example 2 were each added to individual agitated vessels containing 100 mls of artificial sea water. Each zeolite sample contained 0.057 g of pure tributyltin acetate and 0.057 g of pure tributyltin oxide was added to a further 100 ml of agitated, artificial sea water as a control experiment. After 4 hours a filtered sample of sea water from the vessel containing only the tin compound contained 11 ppm by weight of tin which approaches the quoted value of the solubility of the tin compound in water. Sea water samples from the vessel containing the zeolite-impregnated tin compound contained less than 1 ppm of tin after 4 hours and 2 ppm of tin after 70 hrs agitation.

EXAMPLE 5

A series of anti-fouling paints were produced by adding various zeolite/biocide compositions to three different paint bases. The zeolite/biocide compositions were prepared as described in Examples 1 to 3, the biocides which were liquid at room temperature being incorporated by addition of the liquid to the zeolite at room temperature with stirring and any biocides solid at room temperature being heated to liquify them before incorporation. The zeolite was in anhydrous form.

The zeolite/biocide compositions were incorporated into the paints by stirring and the paints then used to coat mild steel test plates. The coated plates were tested for anti-fouling activity by immersion in the sea at a tropical location (Singapore) for 6 weeks and a temperate location (Isle of Wight, England) for 3 months. The plates were assessed visually for fouling using a scale from 0 (no visible fouling) to 10 (100% coverage of plate by fouling).

The components used were:

Paints

Epoxy resin supplied by Shell Chemicals Ltd. under the trade name Epikote 1001.

Epoxy-coal tar resin supplied by Goodlass, Wall Ltd., under the trade name Epotan S.

Chlorinated rubber supplied by Goodlass Wall Ltd., as High Build Chlorinated Rubber.

Zeolite

Zeolite 13X (10 Å pore diameter) supplied by W. R. Grace Ltd., as powder having an average particle diameter of 3-5 microns.

Biocides

Tributyl tin oxide
Tributyl tin acetate
Tributyl tin chloride
Tripropyl tin chloride The components used and the antifouling test results are given in Table 1 below.

TABLE 1

| Paint Base | Zeolite %wt | Biocide Type | %wt | Anti-fouling Rating |
|---|---|---|---|---|
| 1. Tests at Singapore - 6 weeks immersion | | | | |
| Epoxy | — | — | — | 10 |
| Epoxy | 41.2 | Tripropyl tin Chloride | 25.8 | 0 |
| Epoxy-coal tar | 30.1 | Tripropyl tin Chloride | 12.9 | 0 - 1 |
| epoxy-coal tar | 40.1 | Tributyl tin Acetate | 14.4 | 0 |
| Epoxy-coal tar | 28.5 | Tributyl tin Chloride | 16.0 | 0 |
| 2. Tests at Isle of Wight - 3 months immersion | | | | |
| Epoxy-coal tar | — | — | — | 10 |
| Epoxy-coal tar | 22 | Tripropyl tin Chloride | 13 | 0 - 1 |
| Epoxy-coal tar | 22 | Tributyl tin oxide | 13 | 2 - 3 |
| Chlorinated rubber | 22 | Tripropyl tin chloride | 13 | 0 - 1 |
| Chlorinated rubber | 22 | Tributyl tin oxide | 13 | 2 - 3 |
| Commercial anti-fouling paint | — | — | — | 3 - 4 |
| Commercial self-polishing coating | — | — | — | 3 - 4 |

The results in Table 1 show that the control plates using paint without biocide exhibited heavy fouling, thus proving that the test conditions were realistic. The control plates using existing commercial paints also showed moderate fouling. By contrast the plates using paints containing zeolite/biocide compositions all showed anti-fouling activity at least as good as or better than the commercial paints.

EXAMPLES 6, 7, 8

Examples 1, 2 and 3 were repeated using instead of Zeolite 13X, a porous silica sold by Joseph Crosfield and Sons Ltd., under the trade mark "Neosyl" having a specific gravity of 2.0 and a particle size less than 30 microns. As with Examples 1 to 3 all the tributyltin compounds were adsorbed and the mobility of the powder maintained.

EXAMPLE 9

Two aqueous dispersions of wax were produced having the following compositions in percent by weight.

| | 1 | 2 |
|---|---|---|
| Paraffin wax of 60/62° C melting point | 39.0 | 19.5 |
| Montan Wax (LP Wax ex Farbwerke Hoechst) | 5.0 | 4.9 |
| Polyethylene glycol of 1540MW (Carbowax 1540) | 1.0 | 0.49 |
| Stearic acid (Prifac 014) | 2.32 | 2.3 |
| Polyisobutylene of 350$M_n$ (Hyvis 03) | 2.5 | 1.9 |
| 2-ethyl hexanol | 0.1 | 0.32 |
| Triethanolamine | 1.16 | 1.2 |
| Hydroxyethyl cellulose (Cellosize QP 4400L) | 0.02 | 0.3 |
| Zeolite 13X containing tributyl tin oxide | 10.0 | — |
| Silice (Neosyl) containing tributyl tin oxide | — | 4.88 |
| Water | balance | balance |

The dispersion was produced by mixing the components (apart from the triethanolamine) at 80° C. The triethanolamine was added slowly with stirring and the stirring was continued for 20 minutes. The mixture was passed through a Manton-Gaulin homogeniser at 80° C and 2000 psig and then cooled rapidly to 30° C.

The Zeolite 13X was a fine powder as in Example 5 and contained tributyl tin oxide in an amount to give a tributyl tin oxide content of 6.45% wt for the water-free coating. The Neosyl silica was also a fine powder as in Examples 6 to 8 and contained tributyl tin oxide in an amount to give a tributyl tin oxide content of 5.77% wt for the water-free coating.

Test patches of each dispersion were applied to the hull of a 24,000 DWT tanker in dry dock. The test patches were each 4 meters wide, covered the depth of the below water-line surface and were applied on top of anti-fouling paint using Atlas Copco A6F spray units with 0.021 inch, 65° spay tips.

The dispersions sprayed well to give good coverage at a wet film thickness of 400 microns and dried to give clear white films.

Visual underwater inspection of the patches after 3 months of service showed that the patches were in good condition and free of fouling.

We claim:

1. A biocidal composition, suitable for use in marine anti-fouling coatings, comprising particles of a water-insoluble mineral having an internal pore structure and, included within the pores, a biocidal compound effective against marine growth, said water-insoluble mineral selected from the group consisting of zeolites and silicas, said silicas having an average pore diameter of from 10 to 250Å and said biocidal compound being an organo-tin compound of general formula $$R_3SnX$$

where $R$ is a hydrocarbyl group with from 1 to 10 carbon atoms and $X$ is an anion.

2. A biocidal composition as claimed in claim 1, wherein R is alkyl or aryl and X is an oxygen, sulphur, halide or organic acid anion.

3. A biocidal composition as claimed in claim 1, wherein the zeolite is a synthetic faujasite.

4. A biocidal composition as claimed in claim 1, wherein the mineral is in the form of particles having an average particle size below 200 microns.

5. A biocidal composition as claimed in claim 1, wherein the biocidal compound is present in an amount of from 1 to 100% by weight of the mineral.

6. A biocidal composition as claimed in claim 5, wherein the biocidal compound is present in an amount of from 50 to 100% wt by weight of the mineral.

7. In an anti-fouling marine coating containing a film-forming vehicle and a biocide; the improvement consisting of, as the biocide, the composition as claimed in claim 1.

8. An anti-fouling marine coating as claimed in claim 7, wherein the coating contains 5 to 50% wt of mineral and 5 to 30% wt of biocidal compound.

9. An anti-fouling marine coating as claimed in claim 7, wherein the coating contains a wax.